July 23, 1940. C. MAGLIO Plant Pat. 413
PLUM TREE
Filed Feb. 23, 1940
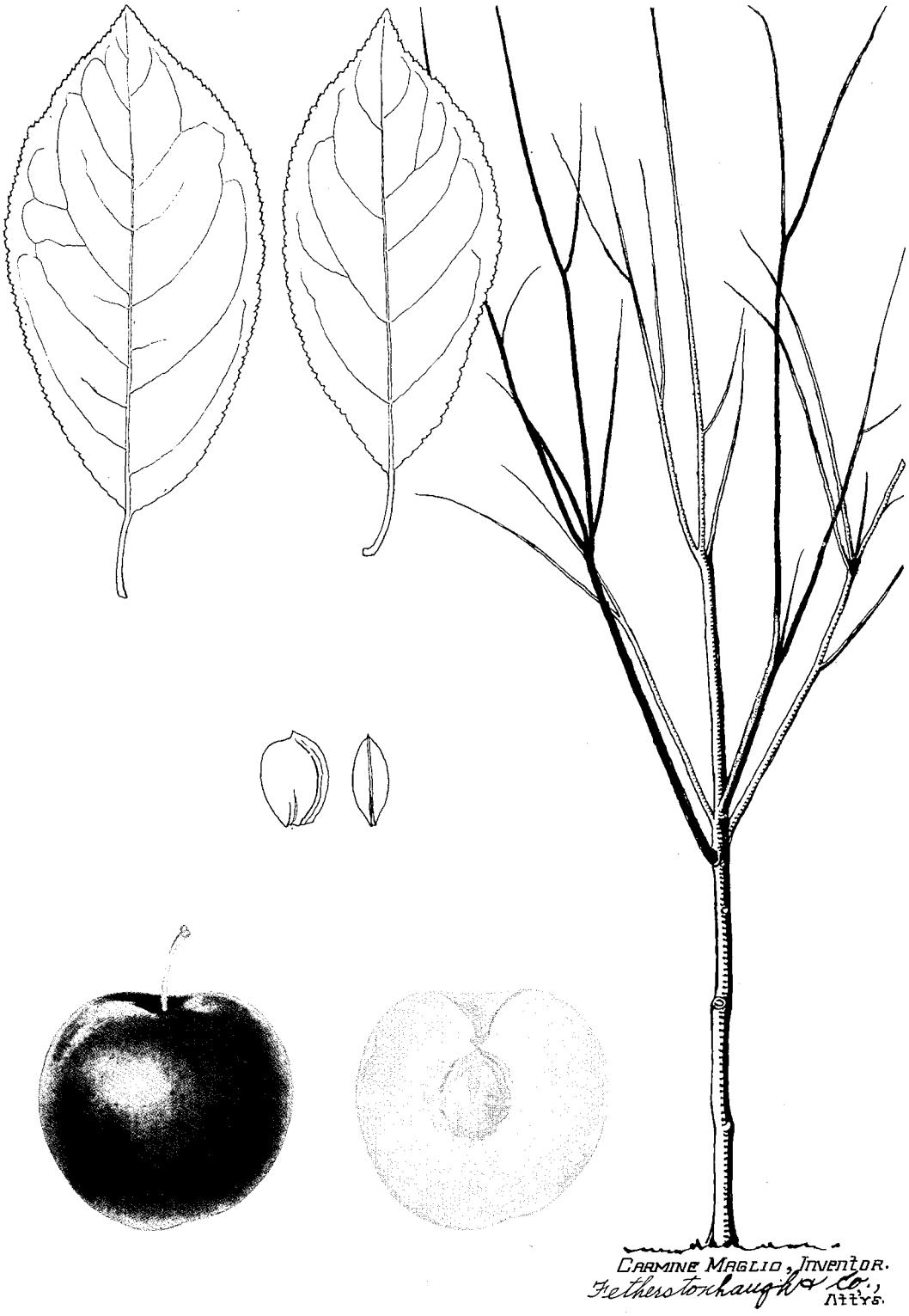

Patented July 23, 1940

Plant Pat. 413

UNITED STATES PATENT OFFICE

413

PLUM TREE

Carmine Maglio, Nelson, British Columbia, Canada

Application February 23, 1940, Serial No. 320,382

1 Claim. (Cl. 47—62)

This invention relates to a variety of plum tree.

The object of the invention was to produce a plum tree with a fruit of good keeping qualities, late maturity, large size and improved flavour, which would be suitable as a dessert plum.

The tree of the invention is the product of a long history of cross breeding.

The variety is principally characterized by the large size, deep rich red colour, late maturity and good keeping and shipping qualities of the fruit.

The following more detailed description refers to and the attached drawing shows the variety as grown in the vicinity of Nelson, in the Province of British Columbia, Canada.

The original drawing illustrates two typical leaves, the stone and the fruit in natural size, and the growth habit of the tree diagrammatically.

The variety forming the subject of this application resembles the Japanese more closely than the European varieties, though, as shown, it is rather more upright in growth than the former. As in the case of the Japanese plum its leaves are, as shown, long and narrow, and their margins are finely serrate. They are on the whole rather like peach tree leaves. The variety flowers generally earlier than the European varieties, about the same time as the Japanese, and has a long growing season. Its flower buds tend to rise from auxiliary buds on young shoots or from very small spurs, in contrast again to the European varieties which produce rather long fruiting spurs.

The tree is annular in habit and is a heavy bearer. Its fruit is late in maturity, October being its season in British Columbia. It has excellent keeping qualities under home conditions without refrigeration, and is of large size, being about two inches or more in diameter and about two inches long. Its shape is round to conic, as shown, and it very often has unequal halves. It has, as shown, a cavity of medium depth and a stem about seven-eighths of an inch long which separates readily. The suture varies from shallow to deep and distinct and the apex is generally round but often pointed. As shown, the skin is of a dark red and very attractive colour with numerous conspicuous dots of ash colour and a whitish heavy bloom. The skin is thin, medium tender and rather sour but separates easily from the flesh. In spite of the thinness of the skin, however, the fruit has good shipping qualities. The flesh is, as shown, of a yellow to deep orange colour and is firm, jelly-like, juicy, and of a sweet to neutral, pleasing flavour.

The variety is of the clingstone type, the stone being flat, of oval shape and deeply ribbed and measuring about three-quarters of an inch in width and nine-sixteenths of an inch in length.

The scions or buds for reproducing the variety should be taken from a fairly old tree, say about ten years.

I claim:

The new variety of plum tree characterized by the deep rich red colour, as shown and described, and the late maturity and good keeping and shipping qualities, as described, of its fruit.

CARMINE his × mark MAGLIO.

Witness to mark:
ERIC P. DAWSON.